United States Patent [19]

Lloyd

[11] Patent Number: 5,510,161

[45] Date of Patent: Apr. 23, 1996

[54] TAPE LAMINATES FOR DIAPER CLOSURE

[75] Inventor: Peter M. Lloyd, Penllergaer, Wales

[73] Assignee: Minnesota Mining and Manufacturing Company, St. Paul, Minn.

[21] Appl. No.: 232,237

[22] PCT Filed: Nov. 4, 1992

[86] PCT No.: PCT/US92/09424

§ 371 Date: May 5, 1994

§ 102(e) Date: May 5, 1994

[87] PCT Pub. No.: WO93/11728

PCT Pub. Date: Jun. 24, 1993

[30] Foreign Application Priority Data

Dec. 17, 1991 [GB] United Kingdom ............... 9126781

[51] Int. Cl.⁶ .................................................. B32B 3/06
[52] U.S. Cl. ............... 428/40; 428/192; 428/194; 428/345; 428/348; 428/352; 428/354; 428/447; 428/452; 428/511; 604/389; 604/390
[58] Field of Search ............... 428/40, 354, 906, 428/194, 192, 352, 345, 348, 447, 452, 511; 604/389, 390

[56] References Cited

U.S. PATENT DOCUMENTS

| | | | |
|---|---|---|---|
| 2,714,889 | 4/1953 | Chambers | 128/287 |
| 2,913,355 | 11/1959 | Collins | 428/352 |
| 3,221,738 | 12/1965 | Ekberg et al. | 128/287 |
| 3,616,114 | 10/1971 | Hamaguchi | 161/39 |
| 3,620,217 | 11/1971 | Gellert | 128/284 |
| 3,932,328 | 1/1976 | Korpman | 260/27 BB |
| 3,951,149 | 4/1976 | Ness et al. | 128/287 |
| 3,987,793 | 10/1976 | Milnamow | 128/287 |
| 3,999,546 | 12/1976 | Feldman et al. | 128/284 |
| 4,020,842 | 5/1977 | Richman et al. | 128/287 |
| 4,133,939 | 1/1979 | Bokerman et al. | 428/447 |
| 4,136,071 | 1/1979 | Korpman | 260/27 BB |
| 4,227,530 | 10/1980 | Schatz | 128/287 |
| 4,641,753 | 2/1987 | Tamada | 209/546 |
| 4,726,971 | 2/1988 | Pape et al. | 428/40 |
| 4,801,480 | 1/1989 | Panza et al. | 428/40 |
| 4,867,828 | 9/1989 | McIntyre | 156/247 |
| 5,023,138 | 6/1991 | McIntyre | 428/352 |
| 5,061,535 | 10/1991 | Kreckel et al. | 428/42 |

FOREIGN PATENT DOCUMENTS 0148587A 12/1984 European Pat. Off. .

*Primary Examiner*—Nasser Ahmad
*Attorney, Agent, or Firm*—Gary L. Griswold; Walter N. Kim; William J. Bond

[57] ABSTRACT

A composite pre-laminated tape is provided having at least one tape backing (13) of a porous paper coated on one face with a release coating (15) of a solventless, radiation-cured silicone applied directly to the paper.

9 Claims, 1 Drawing Sheet

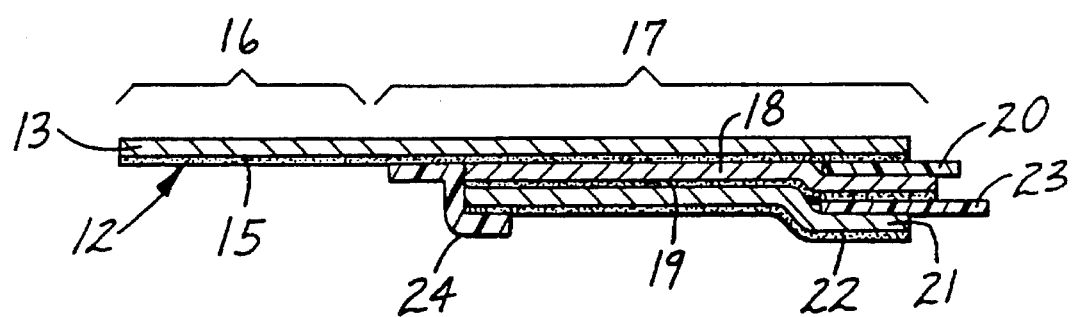

TAPE LAMINATES FOR DIAPER CLOSURE

TECHNICAL FIELD

This invention relates to tape laminates and in particular to composite pre-laminated tapes for forming closures, e.g., for disposable diapers.

BACKGROUND AND FIELD OF THE INVENTION

At least as early as 1955, it had been suggested to use trips of normally tacky and pressure-sensitive adhesive tape to secure conventional cloth diapers on an infant, see for example U.S. Pat. Nos. 2,714,889 and 3,221,738. A few years later, when disposable diapers became extremely popular, strips of pressure-sensitive adhesive tape were again employed as closures, see for example U.S. Pat. No. 3,620,217.

A disposable diaper typically has a thin, flexible, low density polyethylene film cover, an absorbent filler within the cover, and a porous inner liner overlying the filler. The diaper is positioned at the crotch of an infant with the two ends of the diaper extending toward the front and back, respectively. Edges on each side of the diaper are then either positioned adjacent to each other or overlapped using a strip of pressure-sensitive adhesive tape being adhered to the cover film at border regions adjacent each of the two edges to hold the diaper closed.

After a tape closure has been opened, it is frequently discovered that the diaper has not been soiled and hence that there is no need to replace it. If the diaper cover has not been torn, a second strip of tape can sometimes be applied as a replacement closure, but this is often inconvenient. As a result, considerable work has been undertaken to develop a tape diaper closure that is not only capable of bonding firmly to the diaper cover but is also capable of being opened without destroying the tape diaper closure or the diaper cover and subsequently reclosed. Closures of this type have involved a combination of two or more tapes, one of which remains permanently adhered to one edge of the diaper and the other being removably adhered to the other edge of the diaper. Examples of such products are disclosed in U.S. Pat. Nos. 3,951,149, 3,987,793, 3,999,546, 4,020,842, 4,227,530, 4,726,971 and 4,801,480, and European Patent No. 0148587A.

Typically, tape closures for diapers are fabricated by positionably mounting a plurality of individual rolls of the appropriate tapes and combining then in situ to form a composite strip of tape, the width of which is substantially the same as the length of the diaper closure to be fabricated. The composite roll is then severed at right angles to the edges of the composite strip at intervals corresponding to the width of the desired tape closure and adhered at an appropriate location along the border adjacent the side edges of the diaper as exemplified in U.S. Pat. Nos. 3,616,114, 4,726,971 and 4,801,480, and European Patent no. 0148487A. Although this manufacturing process is effective, relatively sophisticated machinery is necessary to accomplish the superimposition of several rolls of tape to form a composite strip of tape in situ. Thus, it is desirable to provide diaper manufacturers with a composite pre-laminated tape in a single roll from which tape closures may readily be prepared.

A common feature of such tape closure systems is that the fastening or closure tape comprises a backing, such as paper, polymeric film etc., having an adhesive layer on one side and a coating of a suitable release agent on the other side to facilitate unwinding of the composite strip when wound upon itself about a core. Generally, the backing comprises paper which is coated with a barrier layer prior to application of the release agent in the form of a solution or water-based formulation. The barrier layer prevents the formulation of release agent being absorbed by the porous paper prior to drying thereby ensuring the release agent remains at the surface where it is most effective. Suitable materials for the barrier layer include polyethylene, typical release agents are based on silicone chemistry.

Solventless, radiation-curable release coating compositions are known and are disclosed, for example, in British patent No. 2010698. The compositions may be applied and cured on any suitable substrate including paper, wood, metals, plastics materials, ceramics, glass, concrete etc. The Examples illustrate the release coating being applied to 40 pound (18 kg) super-calendared kraft paper.

European Patent Application No. 0315297 discloses that in order to employ radiation-curable silicone coatings on porous and lightly moisture-absorbent paper substrates it is necessary to employ a barrier coating or radiation-insensitive hot melt material e.g a wax-like material. The use of the hot melt wax-like material allows poor grade, porous papers to be successfully coated with radiation-curable silicone and pressure-sensitive adhesive tapes may be formed from such release coated paper.

It has now been found that pressure-sensitive adhesive tapes suitable for use in closure systems may comprise a backing of paper coated directly with a solventless radiation-cured release coating.

Therefore, according to the present invention, there is provided a laminate tape construction comprising two or more tapes each having a layer of pressure-sensitive adhesive in which at least one of the tapes comprises a paper backing having, on the opposite side to said adhesive layer, a release coating of a solventless, radiation-cured silicone applied directly to the paper.

The laminate tape construction of the invention is suitable for closure system, particularly for diapers, with at least the fastening tape having the radiation-cured release coating.

The application of the release coating directly to the paper backing has several advantages, including:

1. lower cost backings may be used because of the elimination of one manufacturing process, film extrusion or lamination of the barrier layer and its associated waste.

2. improved degradability due to the elimination of the barrier layer, such as polyethylene, allowing direct access to the paper fibres through the silicone alone.

3. eliminates or reduces need for pretreatment by corona discharge of the paper prior to silicone coating.

4. eliminates the risk of product failure by delamination at the paper barrier layer interface.

The paper backing provides the basic strength of the tape. A clupak paper provides the combination of strength, extensibility or conformability and reasonable tear resistance to suit the needs of the application. The lamination or extrusion of a barrier layer e.g. polyethylene or similar polymer film, to the surface provides solely a non-porous surface for subsequent coatings. It does not materially affect the properties described above.

A suitable paper will typically be bleached for the aesthetic requirements of a hygiene application but an unbleached (brown), semi-bleached (beige or buff) or colored paper would also be functional.

A range of paper basis weight of 50 to 150 g/m² is suitable, typically 80 to 110 g/m².

The elimination of the barrier layer on the paper requires that the release coating laid down must be cured and thus non-migratory in a very short time, before any significant penetration into the paper can occur.

In accordance with the invention, the curing of the solventless silicone begins essentially immediately. If the cure were thermally actuated, a period of 5 to 60 seconds could be necessary to achieve full cross-linking or cure. If, however, the cure is radiation activated, either by electron beam or ultra violet radiation, the curing process will proceed in a fraction of a second. The advantage of this is that the silicone coating will not have a chance to effectively penetrate the paper before being fixed by the cure mechanism. Higher cure rates permit higher run speeds which in turn means the coated paper is transported to the cure module faster thus further reducing the opportunity for absorption. Typical silicone systems are those commercially available from Goldschmidt, Essen of Germany; General Electric of U.S.A; Wacker Chemie of Germany and Dow Corning of U.S.A.

The coating weight of the silicone fluid should be in the range of 0.4 to 2.0 g/m² to provide a continuous coating that satisfactorily permits the subsequent unwinding of a roll of tape whose adhesive is directly in contact with the silicone coating on the lap below.

The coating will be such that when one layer of the finished tape is superimposed upon another, rolled down with a 2 kg or similar weight and then the upper tape layer is peeled away at 180 degrees, the force required shall be between 0.1 and 3.0 newtons per 25 mm width.

The base paper, as supplied in roll form, may be printed with either a full coating to produce a colored surface or with a definitive legend to identify it or its use. Appropriate printing methods include flexography or rotogravure utilizing commercially available water, solvent-based or solventless inks. Subsequently, the printed or unprinted paper may be corona treated if desired to pretreat the surface to be silicone coated.

The silicone coating may then be applied by commercially available coating stations using the principle of multi-roll gravure coating to achieve the low coating weights required. A typical coating station would use from 3 to 6 coating rolls.

As close as possible to the last nip (the coating nip) of the silicone coating station should be the radiation curing station. This station comprises a source of radiation, typically either ultraviolet or electron beam, directed towards the coated web travelling past. In the event of UV-curing, it may be necessary to also have an inert gas atmosphere above the surface to prevent inhibition of cure by atmospheric oxygen. Typically, this atmosphere is nitrogen.

Subsequently, the siliconized paper may be coated with an adhesive mass either by the application of a hot melt adhesive and subsequent cooling or by the application of a solvent based adhesive of sufficiently high solids content and viscosity that the adhesive does not penetrate the paper surface to any significant degree.

This fastening tape produced as above would be slit to the desired size and then combined with one or two other tapes, e.g., a release tape and a target tape optionally together with fingerlift(s) and a centre stripe to form the laminate tape construction. A fingerlift facility may also be obtained by leaving the edge of paper, e.g., 1 to 6 mm, uncoated with adhesive when the fastening tape is formed.

Examples of laminated tape constructions include:

1. A roll of tape comprising an elongate prelaminated tape composite wound convolutely upon itself about an annular core, especially suited for preparing a tape closure for disposable diapers by simply severing said elongate prelaminated tape composite parallel to the axis of the core at intervals corresponding to the predetermined width of said closure, the length of each such closure corresponding to the width of the roll of tape, said prelaminated tape composite comprising in combination:

a. a fastening tape comprising an elongate strip of sheet backing material, having first and second edges, being substantially as wide as said tape composite and having a layer of a first normally tacky and pressure-sensitive adhesive coated over substantially one surface of said backing material.

b. optionally, a layer of a second aggressive, normally tacky and pressure-sensitive adhesive coated over approximately one-third of the layer of said first normally tacky and pressure-sensitive adhesive along the first edge thereof.

c. a fingerlift provided on the first pressure-sensitive adhesive adjacent the second edge thereof.

d. a release tape, having first and second surfaces, the first surface adhered to said first pressure-sensitive adhesive layer.

e. a layer of normally tacky and pressure-sensitive adhesive coated over the second surface of said release tape.

f. a unifying strip centered along the junction of said second adhesive layer and the adhesive layer on said release tape and adhered to said adhesive layers, at least one of said tapes comprising a paper backing having a release coating of solventless, radiation-cured silicone applied directly to the paper. This construction is in accordance with U.S. Pat. No. 4,726,971.

2. A roll of tape comprising an elongated prelaminated tape composite wound convolutely upon itself about an annular core, especially suited for preparing a tape closure for disposable diapers by simply severing said elongated prelaminated tape composite parallel to the axis of the core at intervals corresponding to the predetermined width of said closure, the length of each such closure corresponding to the width of the roll of tape, said prelaminated tape composite comprising in combination:

a. a fastening tape divided into a bonded section and a fastening section with the fastening tape comprising an elongated strip of sheet backing material, having first and second edges, being substantially as wide as said tape composite, and having a first layer of normally tacky and pressure-sensitive adhesive coated over substantially one surface of said backing material.

b. a first fingerlift provided on the first layer of pressure-sensitive adhesive adjacent the second edge thereof.

c. a target tape, having first and second surfaces, the first surface adhered to said first pressure-sensitive adhesive layer.

d. a second layer of normally tacky and pressuresensitive adhesive coated on the second surface of the target tape.

e. a second fingerlift provided on the second layer of normally tacky and pressure-sensitive adhesive.

f. a release tape having first and second surfaces, the first surface adhered to said second pressure-sensitive adhesive layer.

g. a third layer of normally tacky and pressure-sensitive adhesive coated over the second surface of said release tape.

h. a unifying strip centered over said release tape edge and adhered to the third adhesive layer and to the first adhesive layer on the fastening tape by folding under the target tape, at least one of said tapes comprising a paper backing having a release coating of solventless, radiation-cured silicone applied directly to the paper. This construction is in accordance with U.S. Pat. No. 4,801,480.

3. A roll of tape as described in (2) with the exception that the unifying strip is not folded under the target tape.

4. A roll of tape comprising a composite elongate strip of pressure-sensitive adhesive sheet material wound convolutely upon itself about an annular core, especially suited for preparing tape strips to make the tape closure by simply severing said elongate strip of tape at right angles to the axis of the core at intervals corresponding to the predetermined width of said closure, the length of each such closure corresponding to width of the roll of tape, said composite elongate strip of tape characterized by comprising in combination:

a. a fastening tape comprising an elongate strip of sheet backing material, having first and second edges, being substantially as wide as said composite strip, and having a layer of normally tacky an pressure-sensitive adhesive coated over at least substantially the entire width of said backing material.

b. the adhesive of said fastening tape adjacent the first edge thereof contacting and adhered to the back of a pressure-sensitive adhesive target tape.

c. the adhesive of said fastening tape adjacent the second edge thereof contacting and adhered to the back of a pressure-sensitive adhesive release tape, at least one of said tapes comprising a paper backing having a release coating of solventless, radiation-cured silicone applied directly to the paper. This construction is in accordance with European Patent No. 0148587.

BRIEF DESCRIPTION OF THE DRAWING

The invention will now be described with reference to the accompanying drawing which represents a cross-section through a laminate tape construction in accordance with the invention.

DESCRIPTION OF THE PREFERRED EMBODIMENTS

The composite tape is subdivided into bonded section (16) and fastening section (17) and made up of fastening tape (12), target tape (18), release tape (21) and unifying strip (24).

Fastening tape (12) comprises any suitable paper backing (13) provided a release coating of a solventless, radiation-cured silicone applied directly to the paper to facilitate unwinding of the composite tape when wound upon itself about the core. One face of the backing (13) is coated with a layer (15) of a tacky and aggressive pressure-sensitive adhesive. Suitable adhesives include conventional rubber-resin adhesives which have tack characteristics modified by the inclusion of tackifying resins such as the tackifying resins described in U.S. Pat. No. 4,136,071. The aggressive pressure-sensitive adhesives used for layer (15) may also include conventional rubber-resin adhesives modified to have peel strengths between about 6 and 10 newtons per 25 mm, preferably about 8 newtons per 25 mm. A suitable method for measuring the peel strengths of adhesive layers on a steel, polyethylene or polypropylene surface is described in U.S. Pat. No. 4,801,480.

Target tape (18), formed of any suitable tape backing material, is positioned so that it coincides with and covers part of adhesive layer (15). The top surface of target tape (18) is releasably adhered to adhesive layer (15). The bottom surface of target tape (18) is coated with a layer (19) of normally tacky and pressuresensitive adhesive. This adhesive layer (19) must form a strong shear bond to the outer surface of the diaper where it is adhered during use and may be the same as adhesive layer (15).

A first fingerlift (20) is positioned between fastening tape (12) and target tape (18). The first fingerlift (20) is adhered to fastening tape (12) by adhesive layer (15). Fingerlift (20) facilitates the Lifting of fastening tape (12) from the target tape (18).

Release tape (21), formed of any suitable tape backing material, is positioned such that it substantially covers and is adhered to adhesive layer (19). The top surface of release tape (21) may be provided with a coating of release agent so that target tape (18) may be readily separated from release tape (21).

A second fingerlift (23) is adhesively attached to target tape (18) by adhesive layer (19). The fingerlift (23) is attached to an end portion of target tape (18) and facilitates the separation of target tape (18) from release tape (21) in order to allow initial positioning of target tape (18) and fastening tape (12) on the opposed side of the diaper.

Fingerlifts (20, 23) which are typically formed of narrow strips of polymeric film, are adhered to backing (13) and target tape (18) by adhesive layers (15, 19 respectively). The fingerlifts (20, 23) extend outwardly beyond the edge of fastening tape (12) and target tape (18) to permit and facilitate the separation of the various tapes. The separation of fastening tape (12) from target tape (18) is facilitated when it is desired to reopen the diaper closure.

Unifying strip (24), typically formed of a narrow strip of the same material as fingerlifts (20, 23) is positioned between end portions of tape such that its centerline coincides with the junction of target tape (18) and release tape (21) and adhesive layers (15, 19, 22). Thus, one part of unifying strip (24) is adhered to adhesive layer (22) and an approximately equal part is adhered to adhesive layer (15).

U.S. Pat. No. 4,801,480 illustrates the use of closures formed by severing such a composite tape at intervals corresponding to the predetermined width of the closure, parallel to the axis of the tape core.

What is claimed is:

1. A laminate tape construction comprising two or more porous paper backed tapes each of said porous paper backed tapes having a layer of pressure-sensitive adhesive in which at least one of said tapes comprises a porous paper backing without any barrier layer, said at least one tape having two opposite faces, a first face having a first pressure-sensitive adhesive layer adhered directly thereto and a first continuous release coating of a solventless, radiation-cured silicone applied directly to the porous paper backing second face, the penetration of the silicone into the porous paper backing being such that silicone is not on the porous paper backing first face, which paper backing has a basis weight of from 50 to 150 g/m$^2$.

2. The laminate tape construction as claimed in claim 1 wherein said porous paper backed tape laminate comprises (1) a fastening tape, divided into a bonded section and a fastening section, said fastening tape comprising an elongated strip of said porous paper backing, having first and second edges, being substantially as wide as said tape laminate and having a layer of pressure-sensitive adhesive forming said first pressure-sensitive adhesive layer coated over said first face of said fastening tape porous backing, and said first continuous release coating applied over said second face, (2) a target tape, having first and second faces, first and second edges, the target tape first adhered to said first pressure-sensitive adhesive layer, a second layer of pressure-sensitive adhesive coated on the second face of the target tape, (3) a release tape, having first and second faces, the first face adhered to said second pressure-sensitive adhesive layer; a third layer of pressure-sensitive adhesive coated on the second face of said release tape, and (4) a unifying strip centered over an edge of said release tape and adhered to the third pressure-sensitive adhesive layer on said release tape and to the first pressure-sensitive adhesive layer on said fastening tape.

3. A laminate tape construction as claimed in claim 2 in which a first fingerlift is interposed between the first adhesive layer and the target tape at the second edge of said fastening tape and a second fingerlift is interposed between the second pressure-sensitive adhesive layer and the release tape at the second edge of the target tape.

4. A laminate tape construction as claimed in claim 2 in which the porous paper backing of the fastening tape is free from adhesive at the second edge to provide said first fingerlift.

5. A laminate tape construction as claimed in claim 1 in which the paper backing has a basis weight of from 80 to 110 $g/m^2$.

6. A laminate tape construction as claimed in claim 1 in which the coating weight of the release coating is from 0.4 to 2.0 $g/m^2$.

7. A laminate tape construction as claimed in claim 1 in which the pressure-sensitive adhesive is a hot melt adhesive or a solvent based adhesive.

8. A laminate tape as claimed in claim 1 in which the peel strength of the pressure-sensitive adhesive on said silicone release layer is from 0.1 to 3.0 newtons per 25 mm width.

9. A laminate tape as claimed in claim 1 in which the paper backing is colored and/or bears printed indicia.

\* \* \* \* \*